United States Patent [19]
Reddy et al.

[11] Patent Number: 5,482,051
[45] Date of Patent: Jan. 9, 1996

[54] ELECTROMYOGRAPHIC VIRTUAL REALITY SYSTEM

[75] Inventors: Narender P. Reddy; Sujat M. Sukthankar, both of Akron, Ohio

[73] Assignee: The University of Akron, Akron, Ohio

[21] Appl. No.: 209,992

[22] Filed: Mar. 10, 1994

[51] Int. Cl.⁶ ............................................. A61B 5/04
[52] U.S. Cl. ............................................. 128/733; 128/774
[58] Field of Search ................................ 128/733, 745, 128/774, 782

[56] References Cited

U.S. PATENT DOCUMENTS

| | | |
|---|---|---|
| 3,641,993 | 2/1972 | Gaarder et al. . |
| 3,905,355 | 9/1975 | Brudny . |
| 3,916,876 | 11/1975 | Freeman . |
| 4,149,716 | 4/1979 | Scudder . |
| 4,492,233 | 1/1985 | Petrofsky et al. ............. 128/774 |
| 4,611,284 | 9/1986 | McGill et al. ............. 364/417 |
| 4,811,742 | 3/1989 | Hassel et al. ............. 128/733 |
| 4,986,280 | 1/1991 | Marcus et al. ............. 128/774 |
| 5,012,817 | 5/1991 | Zeilinski et al. ............. 128/744 |
| 5,085,225 | 2/1992 | DeLuca et al. ............. 128/733 |
| 5,086,779 | 2/1992 | DeLuca et al. ............. 128/733 |
| 5,212,476 | 5/1993 | Maloney ............. 128/733 |
| 5,216,193 | 6/1993 | Masubuchi ............. 84/600 |

*Primary Examiner*—Max Hindenburg
*Attorney, Agent, or Firm*—Renner, Kenner, Greive, Bobak, Taylor & Weber

[57] ABSTRACT

A finite element model of a structure is manipulated according to electromyographic signal from the musculature of an operator. The resulting forces are fed back to the operator and a display provides visual feedback of the resulting displacements.

11 Claims, 1 Drawing Sheet

ELECTROMYOGRAPHIC VIRTUAL REALITY SYSTEM

BACKGROUND OF THE INVENTION

The present invention relates to interactive computer modelling of real-world structures and particularly to the deformation of modeled objects in response to forces exerted by an operator.

Virtual reality involves the idea of immersing an operator in a world of computer generated dynamically changing images, and allowing the operator to actively modify this virtual environment.

Virtual reality systems have been built that provide operator inputs to the computer created environment by various position sensors. These sensors may be position sensors such as mechanical linkages or optical trackers that determine the location of all or part of the operator's body. In response to these sensors, the computer generated image is manipulated.

These virtual reality systems provide interaction only with the spatial aspect of object orientation in the visual field. Virtual objects move and/or the operator "moves" within the virtual space. Distances, locations and perspectives change according to the operator's inputs.

These systems provide no interaction with the material properties of the objects in the virtual space. For example, the squeezing of objects, a basic tool for exploring physical properties of an object, is not available for virtual objects.

SUMMARY OF THE INVENTION

The present invention allows an operator to "squeeze" virtual objects and see the objects deform and feel the deformation. This substantially increases the capability to provide a more realistic virtual reality. This improved virtual reality can be used, for example, in medical training and in rehabilitation of handicapped individuals.

The invention includes a method of manipulating a simulation of a physical structure in response to an operator having musculature. The method includes detecting an electromyographic signal from the musculature, producing a force signal in response to the electromyographic signal, and applying the force signal to a model of the physical structure. In the preferred embodiment, the model is a finite element model.

The method further includes determining force values and displacements for nodes of the model and providing a visual representation of the model. The representation is deformed in response to the displacements.

In addition, the method can include providing a force to the musculature in response to the force values.

The invention further includes an apparatus for manipulating a simulation of a physical structure in response to an operator having musculature. The apparatus includes a detector for detecting an electromyographic signal from the musculature, a signal processor producing a force signal in response to the electromyographic signal, and a modelling engine containing a model of the physical structure. In the preferred embodiment, the model is a finite element model.

The force signal is applied to the model to determine force values and displacements for the nodes of the model. A visual display displays a representation of the model being deformed in response to the displacements.

The apparatus can also include a force feedback device that provide a force to the musculature in response to the force values.

DESCRIPTION OF THE PREFERRED EMBODIMENTS

Figure 1:
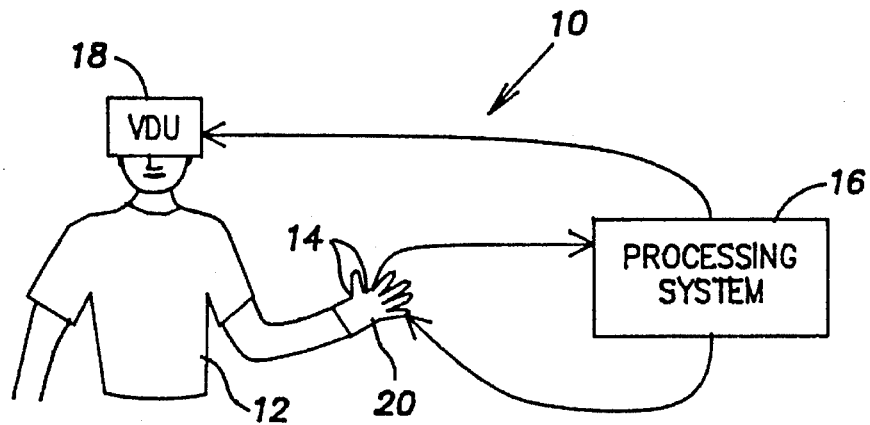
FIG. 1 is a block diagram of a system according to the invention.

Referring to FIG. 1, a virtual reality system 10 is connected to an operator 12 by electromyographic sensors 14.

In the preferred embodiment, the sensors 14 are placed on the back surface of the hand of the operator 12 to monitor the electrical signals of the musculature of the hand, but other portions of the operator's musculature could be monitored if desired. The sensors 14 may be, for example, adhesive-coated electrodes. The sensors 14 are shown connected to a processing system 16, but could be linked instead by a radio or other wireless channel.

A visual display unit 18 is connected to the processing system 16 and provides the operator 10 with a visual display generated by the processing system 16. The visual display unit, may be, for example, a conventional computer graphics monitor or a headmounted virtual reality "helmet." The display unit 18 could also be provided with a wireless link to the processing system 16.

A force feedback unit 20 is connected to the processing system 16 and provides either pressure or other tactile feedback to the operator 12. The unit 20 may be composed, for example, of micro-hydraulic cylinders, inflatable bladders, electric motors/solenoids, shape memory alloys, shape memory polymers or various vibratory devices. The unit 20 could also be provided with a wireless link to the processing system 16.

Figure 2:
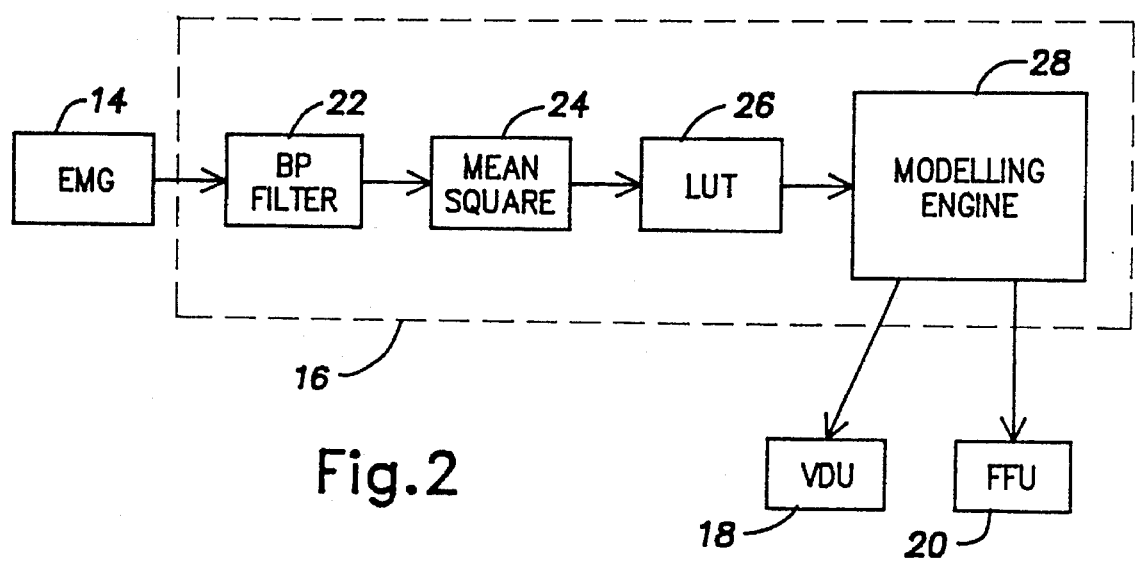
FIG. 2 is a more detailed block diagram of a system according to the invention.

Referring to FIG. 2, the processing system 16 includes a band pass filter 22 connected to the sensors 14. The filter 22 may, for example, pass signals in the 30 to 1,000 hertz range. The output of the filter 22 is connected to a mean-square calculating circuit 24. The filter 22 and circuit 24 may be, for example, either analog circuits, or the signal from the sensors 14 may be digitized and the functions of the filter 22 and circuit 24 performed digitally. When the filter 22 and circuit 24 are implemented digitally, they may be either separate digital signal processing devices or be implemented in a general purpose computer or microprocessor performing other functions in the system 10.

As an alternative, the mean-square calculating circuit 24 can be replaced with a power spectrum and mean power calculating device. It also may be advantageous to use other statistical quantities than mean-square value depending on the nature of the electromyographic signal sensed.

The digitized value of the output of the circuit 24 is used to address a look-up table 26 to determine a corresponding force value. The look-up table 26 may be, for example, implemented in a general purpose computer or microprocessor. The values in the look-up table 26 are predetermined by the operator 10 manipulating or squeezing a force-measuring sensor while the corresponding electromyographic statistical value and measured force are stored in the table 26. The table 10 then contains a range of electromyographic statistical values versus force values that represent a calibration curve for the system 10.

As an alternative, a function for the calibration curve can be determined and forces directly calculated from the electromyographic statistical values.

The force value from the look-up table 26 is provided to a modelling engine 28. The modelling engine 28 contains a finite element model of a physical structure of interest. As is well known in the art, such a model includes a collection of interconnected nodes. The modelling engine 28 provides the forces and displacements associated with each of these nodes. The force information is provided to the force feedback unit 20 and the displacement and node location information are provided to the visual display unit 18.

The engine 28 may be, for example, a general purpose computer or a specialized device for rapidly performing the necessary modelling calculations. It is also possible to model the structure of interest with less computationally demanding (and usually less accurate) models such as wire frame modeling.

In operation, the system 10 is connected to the operator 12. The operator 12 manipulates a virtual object as viewed on the visual display unit 18 and/or felt on the force feedback unit 20. This results in electromyographic signals from the operators musculature being sensed by the sensors 14.

The electromyographic signals are filtered by the filter 22 and their mean-square value determined by the circuit 24.

The mean-square value is used in the look-up table 26 to provide a force value to the modelling engine 28.

The modeling engine 28, which has been preloaded with the finite element model of the object of interest, determines the forces on the nodes of the model and their displacements.

The node forces are used to provide an input to the force feedback unit 20, which in turn provides the "feel" of the object of interest to the operator 10.

The displacement and location the nodes are provided to the visual display unit 18 to show the "deformation" of the object of interest as it is "squeezed" or otherwise manipulated by the operator 12.

While the preceding disclosure deals primarily with a single electromyographic input, it should be understood that this invention is equally applicable to a multitude of such inputs, each being similarly processed.

The system 10 can be used in surgical planning and medical resident training. Three-dimensional images acquired from, for example, x-ray computed tomography or magnetic resonance imaging can provide the necessary information to model an organ or other body structures. The surgeon or student can then practice all or part of a surgical operation.

The "feel" of the physical properties of the modelled structures can be achieved by generating a fine mesh of finite element nodes for each of the structures and assigning the material properties based on the image data. The finite element model can then be manipulated in response to the operator's electromyographic signals.

The system 10 may also be used to restore "feeling" to handicapped individuals. Electromyographic signals from intact muscle groups can be used to control "squeezing" of virtual objects when the individual has no means to actually squeeze a physical object. Visual and force feedback to a functioning pressure sensitive portion of the individual's anatomy allows him to experience the effects of the squeezing.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed:

1. A method of manipulating a computer simulation of a physical structure in response to an operator having musculature, said method comprising:

detecting an electromyographic signal from said musculature; producing a force signal in response to said electromyographic signal;

applying said force to a computer model of said physical structure, said model having nodes;

determining force values and displacements for said nodes; and providing a visual representation of said model, said representation being formed in response to said displacements.

2. A method according to claim 1, wherein said electromyographic signal is from operator hand muscles.

3. A method according to claim 1, wherein said step of producing a force signal includes determining a statistical value of said electromyographic signal and providing a force signal corresponding to said statistical value according to a predetermined calibration curve.

4. A method according to claim 1, wherein said model is a finite element model.

5. A method according to claim 1, further comprising providing a force to said musculature in response to said force values.

6. An apparatus for manipulating a computer simulation of a physical structure in response to an operator having musculature, said apparatus comprising:

a detector for detecting an electromyographic signal from said musculature;

a signal processor producing a force signal in response to said electromyographic signal;

a modelling engine containing a computer model of said physical structure, said model having nodes and said force signal being applied to said model to determine force values and displacements for said nodes; and a visual display, said display displaying a representation of said model being deformed in response to said displacements.

7. An apparatus according to claim 6, wherein said electromyographic signal is from operator hand muscles.

8. An apparatus according to claim 6, wherein said signal processor includes means to determine the mean-square value of said electromyographic signal and a look-up table to provide a force signal in response to said mean-square value.

9. An apparatus according to claim 6, wherein said model is a finite element model.

10. An apparatus according to claim 6, further comprising a force feedback device that provide a force to said musculature in response to said force values.

11. An apparatus for manipulating a computer simulation of a physical structure in response to an operator having musculature, said apparatus comprising:

a sensor connected to said musculature for sensing an electromyographic signal;

a band pass filter communicating with said sensor for filtering said electromyographic signal;

a mean-square calculating device communicating with said filter for determining the mean-square value of said filtered electromyographic signal;

a look-up table communicating with said calculating device, said mean-square value producing a corresponding force signal;

a modelling engine containing a finite element computer model of said physical structure, said model having nodes and said force signal being applied to said model to determine force values and displacements for said nodes;

a visual display communicating with said modelling engine and displaying a representation of said model being deformed in response to said displacements; and a force feedback device communicating with said modelling engine and providing a force to said musculature in response to said force values.

* * * * *